United States Patent
Bartels et al.

(10) Patent No.: US 9,226,829 B2
(45) Date of Patent: Jan. 5, 2016

(54) ROTARY JOINT PROSTHESIS HAVING A REINFORCED BEARING BUSH

(75) Inventors: Carolin Bartels, Barmstedt (DE); Klaus Dmuschewsky, Hamburg (DE); Marco Iredi, Norderstedt (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 14/126,356

(22) PCT Filed: May 8, 2012

(86) PCT No.: PCT/EP2012/058418
§ 371 (c)(1),
(2), (4) Date: Dec. 13, 2013

(87) PCT Pub. No.: WO2012/171722
PCT Pub. Date: Dec. 20, 2012

(65) Prior Publication Data
US 2014/0148913 A1    May 29, 2014

(30) Foreign Application Priority Data
Jun. 16, 2011  (EP) .................................... 11170134

(51) Int. Cl.
*A61F 2/38* (2006.01)
*A61F 2/30* (2006.01)

(52) U.S. Cl.
CPC ............. *A61F 2/3836* (2013.01); *A61F 2/3804* (2013.01); *A61F 2/385* (2013.01); *A61F2002/30354* (2013.01); *A61F 2002/30364* (2013.01); *A61F 2002/30507* (2013.01); *A61F 2220/0025* (2013.01); *A61F 2220/0033* (2013.01)

(58) Field of Classification Search
CPC ........... A61F 2/38; A61F 2/386; A61F 2/384; A61F 2220/0025; A61F 2/3836
USPC ................................ 623/20.14, 20.15, 20.21
See application file for complete search history.

(56) References Cited

U.S. PATENT DOCUMENTS

| 4,538,305 A | 9/1985 | Engelbrecht et al. |
| 4,790,853 A | 12/1988 | Engelbrecht et al. |
| 5,824,102 A * | 10/1998 | Buscayret .................. 623/20.21 |

FOREIGN PATENT DOCUMENTS

| DE | 31 19 841 | 12/1982 |
| DE | 20 2009 001 442 | 5/2009 |

(Continued)

OTHER PUBLICATIONS

International Search Report mailed Jun. 5, 2012, directed to International Application No. PCT/EP2012/058418; 7 pages.

(Continued)

*Primary Examiner* — Jason-Dennis Stewart
(74) *Attorney, Agent, or Firm* — Morrison & Foerster, LLP

(57) ABSTRACT

A joint prosthesis comprises a distal component for anchoring to a first bone, a proximal component for anchoring to a second bone, and a coupling piece that, together with the first component, forms a flexion bearing around a first axis and, together with the second component, forms a rotary bearing formed by the pin and the bearing bush around a second axis oriented transversely to the first axis. The rotary bearing comprises a multi-layer bearing insert, having a sliding sleeve surrounding the pin and a support sleeve that encloses said sliding sleeve and is fastened to the coupling piece by means of a securing element, wherein the securing element comprises an actuation unit within the support sleeve and can be connected to the coupling piece such as to ensure tensile strength by means of two aligned bores in the support sleeve and the coupling piece.

15 Claims, 3 Drawing Sheets

(56) References Cited

FOREIGN PATENT DOCUMENTS

| EP | 0 174 531 | 3/1986 |
| EP | 1 532 945 | 5/2005 |

OTHER PUBLICATIONS

International Preliminary Report on Patentability dated Dec. 17, 2013, directed to International Application No. PCT/EP2012/058418; 9 pages.

* cited by examiner

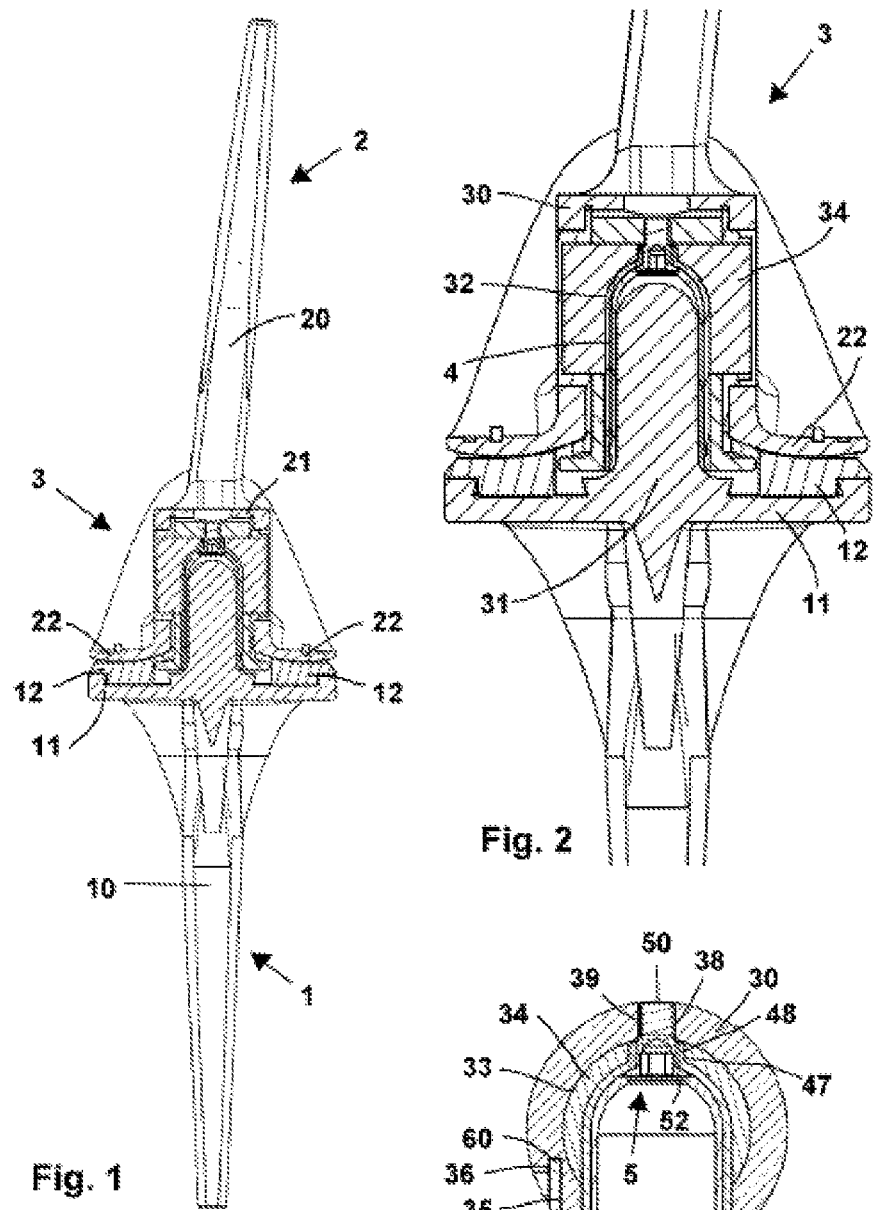
Fig. 1
Fig. 2
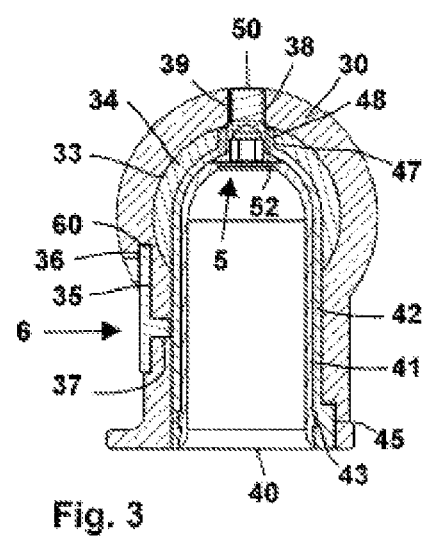
Fig. 3

ROTARY JOINT PROSTHESIS HAVING A REINFORCED BEARING BUSH

REFERENCE TO RELATED APPLICATIONS

This application is a national stage application under 35 USC 371 of International Application No. PCT/EP2012/058418, filed May 8, 2012, which claims priority to European application no. 11170134.8, filed Jun. 16, 2011, the entire contents of which are incorporated herein by reference.

FIELD OF THE INVENTION

The invention relates to a rotary joint prosthesis comprising a distal component and a proximal component, and also a coupling piece which connects said components in an articulated manner and comprises a flexion bearing about a first axis and a rotary bearing about a second axis oriented transversely with respect to the first axis.

BACKGROUND OF THE INVENTION

Prostheses of the aforementioned type are used in particular as knee joint or elbow joint prostheses. Owing to the high load placed on them by the body weight and owing to their complex movement pattern, namely the flexion as the main movement combined with a rotation of the tibia relative to the femur as a secondary movement, knee-joint protheses in particular are relatively susceptible to malfunction due to wear or disease. To treat this, knee joint prostheses are needed that preferably permit both movements, in the interest of restoring the joint function to as close as possible to the anatomical conditions. A further requirement of the joint prosthesis is that it must have sufficient stability, particularly if the support apparatus (ligaments, etc.) composed of soft-tissue parts is already weakened.

In the prior art, various knee prostheses have been disclosed with the aim of combining these partly contradictory objectives of, on the one hand, mobility about two axes and, on the other hand, sufficient stability. In a known rotary knee prosthesis (EP 0174531 B1), a tibial component and a femoral component are connected to each other by a coupling piece, which has an axial eye for receiving an axle carrying a femoral component, in order thereby to create a bending joint. The coupling piece also has a bearing bush which faces toward the tibia and into which a pin arranged on the tibial component engages, in order thereby to form a rotary joint. In order to create favourable friction conditions in this rotary bearing formed by pin and bearing bush, a sliding sleeve made of plastic is arranged in the bearing bush. It is cap-shaped, with a hemispherical top part covering the tip of the pin. The substantially cylindrical jacket bears on the wall of the coupling piece forming the bearing bush. This results in a chambering effect. However, it has been shown that jamming of the bearing sleeve can still occur. For the patient, this defect of the prosthesis generally entails revision surgery.

To overcome this disadvantage, an improved knee-joint endoprosthesis has been made known which is marketed under the name "Endo Modell" by Waldemar Link, Hamburg, Germany. In this, the metal sleeve is designed in two parts, wherein the plastics material providing good sliding properties is enclosed tightly by a shrunk-on metal sleeve with a plurality of drilled holes. The plastics material is better supported by this unit, such that the risk of a defect of the sliding sleeve, particularly on account of cold flow of the plastic as a result of high loading, is greatly reduced. In practice, however, it has been found that the now most important component in the direction of force flow, namely the coupling piece receiving the actual bearing bush, is susceptible to failure as a result of overloading. In a revision of the prosthesis, withdrawal of the bearing bush often proves difficult.

SUMMARY OF THE INVENTION

An object of the invention is to improve a joint prosthesis of the type mentioned at the outset in such a way that it is more robust and, in the event of revision, is easier to disassemble.

A solution according to the invention lies in the features as broadly described herein. Advantageous refinements are the subject matter of the detailed embodiments described below.

In a rotary joint prosthesis comprising a distal component for anchoring in a first bone, a proximal component for anchoring to a second bone, and a coupling piece which, with the first component, forms a flexion bearing about a first axis and, with the second component, forms a rotary bearing, formed by pin and bearing bush, a second axis oriented transversely with respect to the first axis, and a sliding sleeve surrounding the pin, and a support sleeve that completely encloses said sliding sleeve and is fastened to the coupling piece by a securing element, are arranged in the bearing bush, wherein provision is made, according to the invention, that the securing element has an actuation member within the support sleeve and can be connected to the coupling piece such as to ensure tensile strength via two aligned bores in support sleeve and coupling piece.

An aspect of the invention is the concept of positioning the actuation member for the securing element in the interior of the bearing bush. In contrast to the closest prior art, access to the securing element does not then have to be made from the outside through the coupling piece, for which purpose a corresponding opening was needed in the coupling piece, which caused weakening of the latter. By virtue of the actuation member being moved to the inside according to the invention, the opening on the coupling piece can be made much smaller, for which reason it gains stability. Moreover, the securing element can thus engage directly on the bearing bush, such that it can be safely withdrawn even if it is sitting quite firmly in place. This creates the conditions for strengthening the support sleeve by thicker material and even introducing it into the load flow, which leads to correspondingly less stress on the sliding sleeve usually made of plastics material. In this way, greater loads can also be safely taken up, and the danger of defects as a result of overloading decreases. Thicker material of the support sleeve is understood here as meaning that the material thickness is at least 0.8 times the material thickness of the sliding sleeve.

An access opening to the actuation member is preferably provided on the sliding sleeve. In this way, the actuation member lies behind the sliding sleeve, as seen from the admission side of the pin, and can carry this sliding sleeve with it when the securing element is loosened. Thus, the securing element with its actuation member acts at the same time as a remover for the sliding sleeve. Even damaged sliding sleeves, in particular due to jamming or cold flow of the plastics material on overloading, can be easily removed. A particularly expedient design of the securing element is a screw, of which the head forms the actuation member. It is thus possible, by structurally simple means, on the one hand to ensure firm securing in the assembled state, while on the other hand a considerable pressure can be applied to the sliding sleeve by turning the screw, by virtue of the force transmission acting through the thread. Here, the width of the access opening is expediently smaller than the width of the head of the screws. It has proven useful if the access opening of the sliding sleeve widens toward the support sleeve. This provides a conicity that promotes separation by pressure.

Bores of different widths for the securing element are preferably formed in the support sleeve, on the one hand, and in the coupling piece, on the other hand. A stepped bore of this kind has the advantage that the securing element can be inserted with its shank through the support sleeve until it bears via its head. In the screw of a securing element, this means that the diameter of the bore in the support sleeve is greater than the shank diameter of the screw but smaller than the diameter of the head, and that the bore on the coupling piece has a further corresponding core diameter of the screw, and an internal thread is formed on the bore.

In this way, a secure positioning can be achieved by tightening the securing element, in particular by tightening the screw, wherein loosening not only cancels the securing but also allows the sliding sleeve to be pressed out.

To allow a support sleeve that is stuck in place to be easily and safely removed in a revision procedure, a seat for an extractor can be provided on it, preferably flush with the access opening. It has proven particularly useful to design the seat as an internal thread in the bore for the securing element. In this way, after removal of the securing element, the support sleeve can be easily withdrawn from the coupling piece by introducing the extractor and connecting the latter to the support sleeve. For this purpose, in the case of the internal thread design, the extractor need only have a corresponding mating thread at its tip, which mating thread is connected to the support sleeve simply by being screwed in.

Advantageously, the sliding sleeve is secured against an axial movement out of the support sleeve by locking lugs, which are arranged in the area of its pin-side mouth and which engage in an undercut on the inner face of the support sleeve. This counteracts damage caused by luxation movement.

Advantageously, the support sleeve is provided with a radially projecting ledge, which engages in a recess of complementary shape on the coupling piece. This ensures that the support sleeve is not undesirably entrained in the rotation movement about the pin. Since the lug and the recess are arranged at the pin-side end, the form-fit connection can be achieved by simple insertion of the support sleeve into its bearing bush on the coupling piece. Otherwise, the seat for the support sleeve is preferably designed with a smooth wall and with in particular a cylindrical internal shape on the coupling piece. This is simple to produce and provides a uniformly stable bearing, even in the event of an axial movement of the pin in the bearing bush.

In a particular embodiment, the front face of the coupling piece is provided with a receiving surface for an impact-protection means, which is continued by a pocket-like recess into the area of a receiving eye. The impact-protection means functions as a limit stop for the flexion movement, specifically for the extended position. Since the coupling piece can here abut on the distal component, the impact-protection means serves to protect the coupling piece against damage. In order to remain in its intended position in the event of abrupt loading, a sufficiently secure fastening is necessary. By means of the pocket-like recess, it is possible in a simple way to ensure that the impact-protection means is prevented from lifting and falling away from its position on the front face of the coupling piece. Advantageously, the pocket-like recess has a rectangular cross section and merges flat into the receiving surface. In this way, the impact-protection means can be designed as a continuous small plate, which is fixed in its position by pushing in the pocket-like recess. In order to avoid undesired movement out of the pocket-like recess, a depression or a maximum of two depressions are preferably provided on the front face in the coupling piece, which depressions function to secure against movement, particularly with a projection arranged on the rear face of the impact-protection means. In this way, not only is the impact-protection means fastened in a simple to assemble and reliable manner, but the fastening arrangement also avoids undesired weakening of the coupling piece.

BRIEF DESCRIPTION OF THE DRAWINGS

The invention is explained in more detail below with reference to the attached drawing, in which an advantageous illustrative embodiment is depicted. In the drawing:

FIG. 1 shows a rear view of a joint prosthesis in a partially sectioned representation;

FIG. 2 shows an enlarged rear view of the coupling piece with an adjoining component;

FIG. 3 shows a detail of the bearing bush from the side, in a sectioned representation;

DETAILED DESCRIPTION OF THE INVENTION

Figure 4:
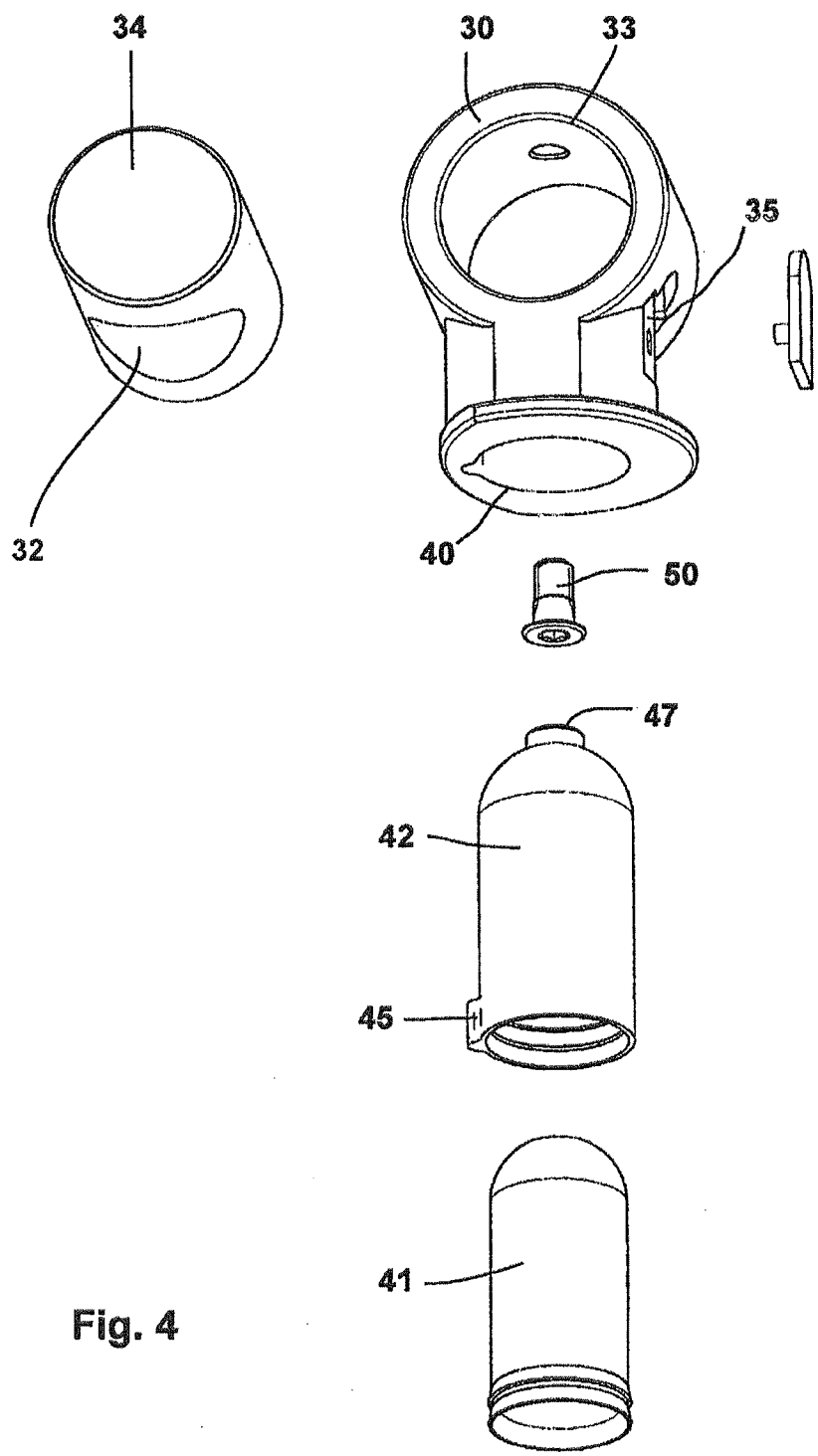
FIG. 4 shows an exploded view of the coupling piece with the bearing bush.
Figure 5:
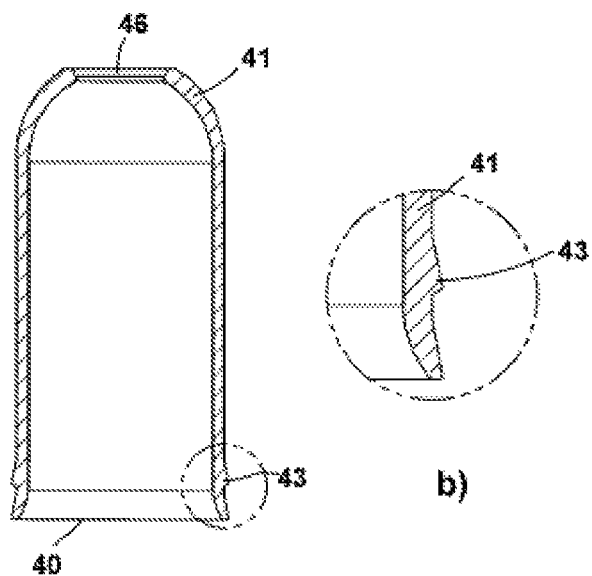
FIGS. 5a, b show details of a locking mechanism.
Figure 6:
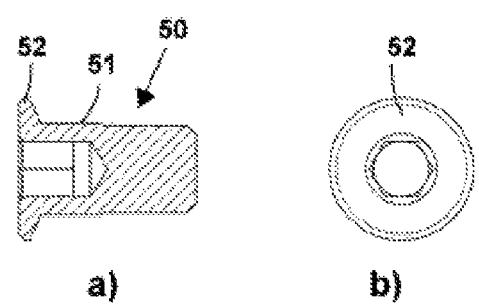
FIGS. 6a, b show details of a securing element.
Figure 7:
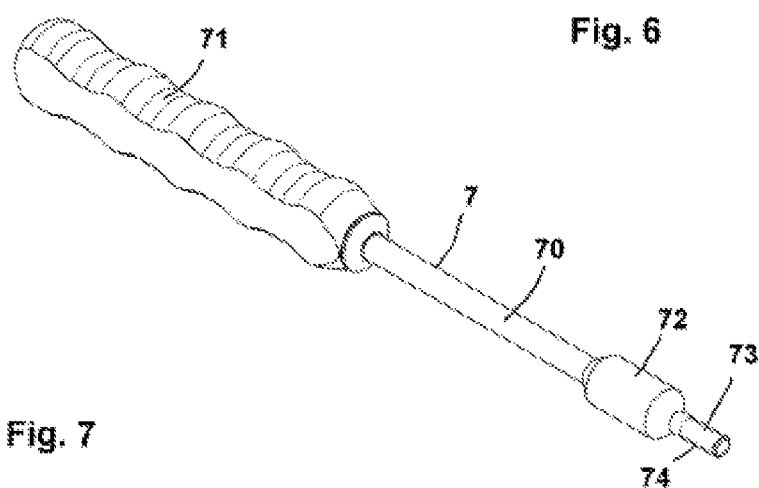
FIG. 7 shows an extractor.

The endoprosthesis according to an illustrative embodiment of the invention is explained on the basis of a knee-joint endoprosthesis.

The endoprosthesis of a knee joint is composed principally of two components 1, 2, of which one is formed as a tibial component 1 and the other as a femoral component 2. In the femoral component 2, a stem 20, which is inserted into a femur of a patient, is adjoined by a femoral bearing half 21, which has two condyle-like runners 22 projecting like a fork toward the tibial component 1. These runners 22 are supported on a tibial plateau 12, which is arranged on a tibial bearing half 11, the latter being fastened by a stem 10 to a tibia of the patient.

Arranged between them is a coupling piece 3, which has a T-shaped piece 30 as a main body with a receiving eye 33 arranged in its upper area for an axial pin 34, and with a bearing bush 32 for a bearing pin 31 rising from the tibial plateau 11.

The first bearing (flexion bearing) permits a pivoting movement between the components 1 and 2 and thus provides a flexion movement between upper leg and lower leg. This pivoting movement about the axis of the axial pin 34 thus forms the first axis for the movement of the knee-joint endoprosthesis. Arranged transversely with respect to this axis is the pin 31, which forms a second axis for a rotation movement, by which the femoral component 2 turns relative to the tibial component 1 about the second axis.

For this rotation bearing, the pin 31 protrudes into the bearing bush 32 on the coupling piece 3. Arranged between both is a bearing insert 4. The latter is fastened in the receiving eye 33 by a securing element 5, in the form of a screw 50, located at the upper end thereof.

The bearing insert 4 is of a substantially cylindrical basic shape and has, at its upper end, a hemispherical dome. The bearing insert 4 is composed of a sliding sleeve 41 and of a support sleeve 42. The external diameter of the bearing sleeve 41 is chosen so as to allow an easy press fit in the inner wall of the support sleeve 42. At its lower end, the support sleeve 41 has a mouth 40 for admission of the pin. Arranged on the inner face, a fixing element 43 extends about the circumference, said fixing element preferably being continuous, although it can also be interrupted several times. It engages in a correspondingly shaped undercut (as seen from the mouth 40 of the bearing insert 4) and thus secures the sliding sleeve 41 against migration from the support sleeve 42. On its outer face at the end toward the mouth, the support sleeve 42 has a radially projecting ledge 45, which engages with positive locking in a recess of complementary shape on the inner face of the bearing bush 32 of the coupling piece 3. In this way, the support sleeve 42 is protected against undesired rotation relative to the coupling piece 3.

The components of the bearing insert 4, that is to say the support sleeve 42 and the sliding sleeve 41, extend as far as the mouth 40 of the bearing insert 4, i.e. both form, with their lower end face, the edge of the mouth 40. The sliding sleeve 41 can be provided with a conically tapering shape on the inner face of the sliding sleeve 41. It facilitates the insertion of the pin 31 into the bearing insert 4.

At its upper end, the sliding sleeve 41 has an access opening 46. This is provided with a conical edge face, of which the width increases toward the top. A first bore 47 in the support sleeve 42 and a second bore 38 in the receiving eye 33 are provided flush with the access opening 46, and the second bore 38 is provided with an internal thread 39. An internal thread 48 is arranged in the bore 47 of the support sleeve 42. The screw 50 is inserted as a securing means into these bores, its shank 51 being screwed into the internal thread 39. The head 52 of the screw 50 has a larger diameter than the width of the access opening 46. It lies firmly on the inner face of the support sleeve 42 and secures the latter in its position.

On its front face (to the right in the view in FIG. 3), the coupling piece 3 is provided with a plane receiving surface 35. At the upper end thereof, a pocket 36 is formed in the receiving eye 33, which pocket 36, at its bottom, merges flat into the receiving surface 35. In the middle area of the receiving surface 35, a retention opening 37 is provided, which is designed as a continuous opening in the bearing bush 31 as far as the support sleeve 42. An impact-protection plate 6 is fitted onto the receiving surface 35, its upper edge being pushed into the pocket 36. By being pushed with its upper edge 60 into the pocket 36, it is secured against lifting away from the receiving surface 35, in particular under the effect of a force from the front (from the right in FIG. 3) when the stop position is reached. In order to avoid movement, particularly downward movement, of the impact-protection plate 6, the rear face thereof is formed with a projection 62, which engages with positive locking in the retention opening 37 and thus secures the impact-protection plate 6 in its position.

An extractor 7 is also provided, which is designed as a screwdriver with a shaft 70 on the handle 71 at its rear end. Arranged at the front end is a guide barrel 72, which has a larger diameter than the shaft 70, and of which the diameter is adapted to the inside width of the bearing insert 4. Adapted is understood here as meaning that it is smaller by approximately 1 mm, such that a clearance fit is obtained. In the front area of the guide barrel 72, a screw tip 73 is arranged that has an external thread 74. This is designed such that it engages in the internal thread 48 in the bore 47.

The bearing insert 4 is fixed in the assembled state by the securing screw 50 of the securing element 5 being screwed in. The securing screw 50 lies with its head 52 on the inner face of the support sleeve 42 and draws the latter against the axial pin 34 mounted in the axial eye 33. The bearing insert 4 is thus secured against movement out of the bearing bush 32.

For disassembly, after the pin 31 has been withdrawn from the bearing bush 32, the securing screw 50 is released in a manner known per se by means of a screwdriver (not shown). Since the head 52 of the screw 50 has a greater width than the through-opening 46 in the sliding sleeve 41, the screw 50 presses the sliding sleeve 41 downward out of the support sleeve 42 with its head 52. The pressing out can be aided by pressing together the sliding sleeve 41 in the area of the mouth 40, to make it easier to disengage the locking elements 43, 44. In many cases, the support sleeve 42 can then be removed from the bearing bush 32. However, if it sits firmly in place, as can easily happen in particular after overloading or after a prolonged period of use, it is possible, after removal of the securing screw 50, to introduce the guide barrel 72 of the extractor 7 into the interior of the support sleeve 42, and the thread 74 on the screw tip 73 of the extractor 7 can be screwed into the internal thread 48 of the support sleeve 42. In this way, the extractor 7 is connected to the support sleeve 42 in a manner ensuring tensile strength, and the latter can be withdrawn from the bearing bush 32.

By virtue of the invention, only a relatively small access hole in the form of the bore 38 in the coupling piece is needed. The rest of the coupling piece can be made solid, i.e. no further interruptions are needed particularly in the area of the receiving eye 33. A weakening of the receiving eye 33 is thus avoided. At the same time, the invention permits a secure fastening of the bearing insert 4 and a simple withdrawal. Arranging the impact-protection plate 6 in the pocket 36 likewise avoids a weakening of the kind that has occurred in the prior art as a consequence of a large number of adhesion holes in the area of the receiving surface 35.

The invention claimed is:

1. A rotary joint prosthesis comprising a first component for anchoring to a first bone, a second component for anchoring to a second bone, and a coupling piece which, with the first component, forms a flexion bearing about a first axis and, with the second component, forms a rotary bearing, formed by a pin and bearing bush, about a second axis oriented transversely with respect to the first axis, wherein the rotary bearing comprises a multi-layer bearing insert with a sliding sleeve surrounding the pin and a support sleeve that encloses said sliding sleeve and is fastened to the coupling piece by a securing element, wherein the securing element has an actuation member within the support sleeve and is configured to be connected to the coupling piece to ensure tensile strength via two aligned bores in the support sleeve and the coupling piece.

2. The rotary joint prosthesis of claim 1, wherein the access opening to the actuation member is provided on the sliding sleeve.

3. The rotary joint prosthesis of claim 2, wherein a seat for an extractor is provided on the support sleeve and is flush with the access opening.

4. The rotary joint prosthesis of claim 3, wherein the seat is configured as an internal thread.

5. The rotary joint prosthesis of claim 2, wherein the actuation member has a greater width than the access opening.

6. The rotary joint prosthesis of claim 5, wherein the access opening tapers inward.

7. The rotary joint prosthesis of claim 1, wherein the securing element comprises a screw, of which the head forms the actuation member.

8. The rotary joint prosthesis of claim 1, wherein the bores have stepped widths.

9. The rotary joint prosthesis of claim 1, wherein the sliding sleeve is secured against an axial movement by a fixing element, which is arranged in an area of a receiving opening of the sliding sleeve and which engages in an undercut on an inner face of the support sleeve.

10. The rotary joint prosthesis of claim 1, wherein a radially projecting lug is provided on the outside of the support sleeve and engages in a recess of complementary shape on the coupling piece.

11. The rotary joint prosthesis of claim 1, wherein the bearing bush is configured with a smooth wall.

12. The rotary joint prosthesis of claim 11, wherein the bearing bush is configured with a cylindrical internal shape.

13. The rotary joint prosthesis of claim 1, wherein, on the front face of the coupling piece, a receiving surface is provided for an impact-protection member, and a pocket-like recess is formed for the continuation thereof.

14. The rotary joint prosthesis of claim 13, wherein the pocket-like recess has a rectangular cross section and merges flat into the receiving surface.

15. The rotary joint prosthesis of claim 13, wherein a maximum of two depressions are provided to secure the impact-protection means against movement.

\* \* \* \* \*